United States Patent
Manfredi

(10) Patent No.: US 11,255,352 B2
(45) Date of Patent: Feb. 22, 2022

(54) TRANSMISSION SYSTEM

(71) Applicant: University of Dundee, Dundee (GB)

(72) Inventor: Luigi Manfredi, Dundee (GB)

(73) Assignee: UNIVERSITY OF DUNDEE, Dundee (GB)

( * ) Notice: Subject to any disclaimer, the term of this patent is extended or adjusted under 35 U.S.C. 154(b) by 99 days.

(21) Appl. No.: 16/618,648

(22) PCT Filed: Jun. 1, 2018

(86) PCT No.: PCT/GB2018/051509
§ 371 (c)(1),
(2) Date: Dec. 2, 2019

(87) PCT Pub. No.: WO2018/220399
PCT Pub. Date: Dec. 6, 2018

(65) Prior Publication Data
US 2021/0140451 A1     May 13, 2021

(30) Foreign Application Priority Data
Jun. 2, 2017     (GB) ...................................... 1708807

(51) Int. Cl.
*F15B 7/08*     (2006.01)
(52) U.S. Cl.
CPC ...................... *F15B 7/08* (2013.01)
(58) Field of Classification Search
CPC ........................................................ F15B 7/08
See application file for complete search history.

(56) References Cited

U.S. PATENT DOCUMENTS

| 2,927,432 A | 3/1960 | Parry | |
| 10,921,164 B2* | 2/2021 | Quartiroli | ............... B81B 7/008 |
| 2015/0113976 A1* | 4/2015 | Bachmaier | ................ F15B 7/08 |
| | | | 60/545 |

(Continued)

FOREIGN PATENT DOCUMENTS

| DE | 102014219884 | 4/2016 |
| WO | 03051218 | 6/2003 |
| WO | 2011094269 | 8/2011 |

OTHER PUBLICATIONS

PCT International Search Report issued for corresponding International Application No. PCT/GB2018/051509, dated Sep. 21, 2018.

(Continued)

*Primary Examiner* — Abiy Teka
*Assistant Examiner* — Daniel S Collins
(74) *Attorney, Agent, or Firm* — Myers Bigel, P.A.

(57) ABSTRACT

A transmission system (10) includes a first piston (12), a second piston (14) and a modulator piston (16). The first piston (12) receives an input force ($F_{IN}$), the second piston (14) transmits an output force ($F_{OUT}$), and the modulator piston (16) transmits a modulating force ($F_{ACT}$) which modulates the input force ($F_{IN}$) received by the second piston (14) to implement tremor cancellation and force and/or provide variable motion scaling.

15 Claims, 4 Drawing Sheets

(56) References Cited

U.S. PATENT DOCUMENTS

2017/0227023 A1* 8/2017 Bachmaier ............ F15B 15/149
2019/0145432 A1* 5/2019 Bachmaier ................ F15B 7/08
              60/545

OTHER PUBLICATIONS

PCT Written Opinion of the International Searching Authority issued for corresponding International Application No. PCT/GB2018/051509, dated Sep. 21, 2018.

* cited by examiner

TRANSMISSION SYSTEM

RELATED APPLICATIONS

This application is a 35 U.S.C. § 371 national stage application of PCT Application No. PCT/GB2018/051509, filed on Jun. 1, 2018, which claims priority from Great Britain Patent Application No. 1708807.1, filed on Jun. 2, 2017, the contents of which are incorporated herein by reference in their entireties. The above-referenced PCT International Application was published in the English language as International Publication No. WO 2018/220399 A1 on Dec. 6, 2018.

FIELD

This relates to a transmission system, in particular, but not exclusively, a hydraulic transmission system for use in a micromanipulator system.

BACKGROUND

A variety of tasks involve micromanipulation, that is the micro scale manipulation of an object with a degree of precision which is difficult or impossible to achieve by the human body unaided. A number of surgical procedures, for example, involve micromanipulation, with the ability to manipulate objects with a high level of control being critical to the success of the given procedure.

In addition to the existing limitations of micromanipulation, a major limiting factor in the adoption of microsurgery techniques and equipment is the presence of physiological tremors, that is the unintentional movement of the user due to involuntary muscle contraction and relaxation. Physiological tremors generally cannot be observed with the naked eye, and are of insignificant consequence in normal day life. However, it will be recognised that during tasks such as microsurgical procedures which require a high degree of accuracy, such physiological tremors are often crucial to the success of the procedure.

With the development of robotics, a number of different equipment and tools have been developed with the aim of reducing the effects of physiological tremor during surgical operations, including intelligent microsurgical instruments and "steady-hand" robotic systems.

However, there remain drawbacks with conventional equipment and techniques. For example, current robotic systems used in surgery either entirely lack or provide very limited haptic feedback to the user, such that delicate surgical tasks cannot be performed effectively and reliably.

SUMMARY

According to a first aspect, there is provided a transmission system, comprising:
an input piston configured to receive an input force;
a modulator piston operatively associated with the first piston and configured to modulate the input force; and
an output piston operatively associated with the first piston and the modulator piston, the output piston configured to receive the modulated input force and output an output force from the transmission system.

Embodiments of the transmission system beneficially permit the ratio of the input force to the output force and the resulting relative motion of the input piston and the output piston to be scaled, whilst also cancelling or at least mitigating the effect of a tremor applied to the input piston or otherwise contained in the input force applied to the input piston. Embodiments of the transmission system thus provide significant improvements in the accuracy and safety of surgical procedures, and may permit surgical procedures to be carried out where such procedures were previously not possible due to the effects of tremors.

In use, the transmission system may convert an input force or motion applied to the input piston into a smaller output force or motion at the output piston, the ability to modulate the input force permitting a variable ratio of the input force and the output force to be achieved; in contrast to conventional systems which are limited to a constant ratio.

The transmission system may be configured to modulate the input force by attenuating or dampening the input force to provide a reduced output force and/or reduced displacement of the output piston.

However, it will be recognised that the transmission system may alternatively modulate the input force to provide an increased output force from the output piston and/or increased displacement of the output piston where required.

The transmission system may comprise or take the form of a fluid transmission system, in particular but not exclusively a hydraulic transmission system.

Beneficially, by providing a hydraulic transmission system which utilises incompressible or substantially incompressible hydraulic fluid, such as hydraulic oil, the user is provided with haptic feedback from the output piston at the input piston, without the use of a complex system of sensors and actuators. The user may thus "feel" any external forces applied to the output actuator and adjust the input force accordingly.

The ability to achieve haptic feedback, for example, facilitates delicate remote or robotic surgical tasks to be performed effectively and reliably.

The transmission system may comprise an input actuator.
The input piston may form part of the input actuator.
The input actuator may comprise a cylinder for housing the input piston.
The transmission system may comprise an output actuator.
The output piston may form part of the output actuator.
The output actuator may comprise a cylinder for housing the output piston.
The transmission system may comprise a control actuator.
The modulator piston may form part of the control actuator.
The control actuator may comprise a cylinder for housing the modulator piston.
The transmission system may comprise a chamber.
The chamber may communicate with the input piston, the output piston and the modulator piston.
The chamber may comprise a sealed chamber for containing the fluid, such as the hydraulic fluid.
The transmission system may comprise a manifold.
The chamber may be formed or provided in the manifold.
The input actuator, the output actuator, the control actuator and the manifold may comprise separate components.
Alternatively, the input actuator, the output actuator, the control actuator and the manifold may be integrally formed.

As described above, the modulator piston is operatively associated with the first piston and configured to modulate the input force.

A force ("modulator force") applied to the modulator piston may modulate the input force. For example, reconfiguring the control actuator by extending the modulator piston may modulate the input force by decreasing the input force, thereby providing a reduced modulated input force to the output piston.

Alternatively or additionally, reconfiguring the control actuator by retracting the modulator piston may modulate the input force by increasing the input force, thereby providing an increased modulated input force to the output piston.

The transmission system may be configured to maintain the ratio of the input force to the output force at a given value or valve range.

It will be recognised that the ratio of the input force to the output force may thus be varied up or down by reconfiguring the control actuator, permitting the scaling of the ratio of the input force and the output force to be varied and/or permitting the effect of a tremor contained within the input force to be cancelled, mitigated or otherwise controlled within a given acceptable range.

The transmission system may comprise a drive arrangement configured to move and/or control the displacement of the modulator piston.

The drive arrangement may comprise a motor.

The drive arrangement, e.g. motor, may be incapable of being back-driven. Beneficially, this may prevent back-lash which may otherwise detrimentally effect the micromanipulation operation. The motor may for example comprise a strain wave gear drive, although other suitable drive may be selected.

The transmission system may comprise, may be coupled to or operatively associated with a control system.

The control system may comprise one or more sensor.

The transmission system may comprise one or more position sensor associated with at least one of the input actuator, output actuator and control actuator.

The position sensor, or at least one of the position sensors where more than one position is provided, may be a magnetic sensor.

The position sensor, or at least one of the position sensors where more than one position is provided, may be a linear encoder.

In use, the control actuator may be controlled according to the sensed position of each actuator.

The transmission system may comprise one or more pressure sensor.

The one or more pressure sensor may be configured to measure the fluid pressure in the chamber.

The transmission system may comprise one or more temperature sensor configured to measure the temperature in the chamber.

According to a second aspect, there is provided an apparatus comprising the transmission system of the first aspect.

The apparatus may comprise an instrument.

The output piston may be coupled to the instrument.

In use, the output actuator may be configured to transfer the output force to the instrument.

The instrument may comprise a surgical instrument, in particular but not exclusively a surgical instrument for use in minimally invasive or laparoscopic surgery.

According to a third aspect, there is provided a method comprising:

providing a transmission system according to the first aspect;

applying a modulating force to the modulating piston to modulate the input force received by the output piston and thereby vary the output force from the transmission system.

It will be understood that the features defined above or described below in relation to specific embodiments may be utilised either alone or in combination.

BRIEF DESCRIPTION OF THE DRAWINGS

These and other aspects will now be described by way of example only with reference to the accompanying drawings, of which.

DETAILED DESCRIPTION

Figure 1:
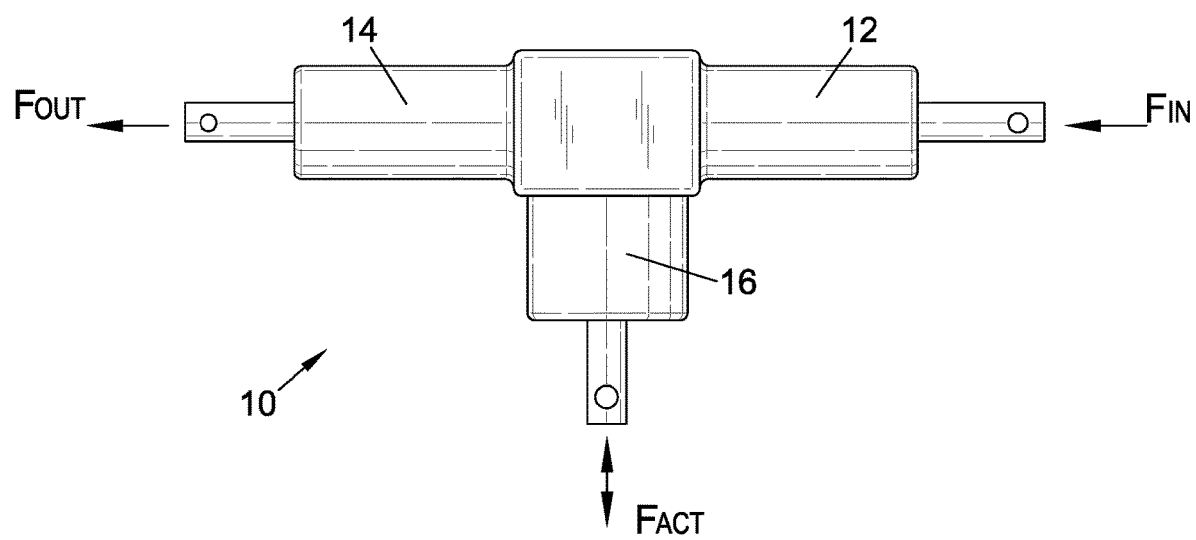
FIG. 1 shows a transmission system.

Referring to FIG. 1 of the accompanying drawings, a transmission system 10 includes a first piston 12, a second piston 14 and a modulator piston 16. The three pistons act as actuators to transmit forces. The first piston 12 transmits an input force $F_{IN}$, the second piston 14 transmits an output force $F_{OUT}$, and the modulator piston 16 transmits a modulating force $F_{ACT}$, as shown in FIG. 1. The transmission system can implement tremor cancellation and motion scaling by enhancing the input force $F_{IN}$ using the modulating force $F_{ACT}$, resulting in the output force $F_{OUT}$. The input force $F_{IN}$ is enhanced by actuation of the modulator piston (16) to control the modulating force $F_{ACT}$.

Figure 2:
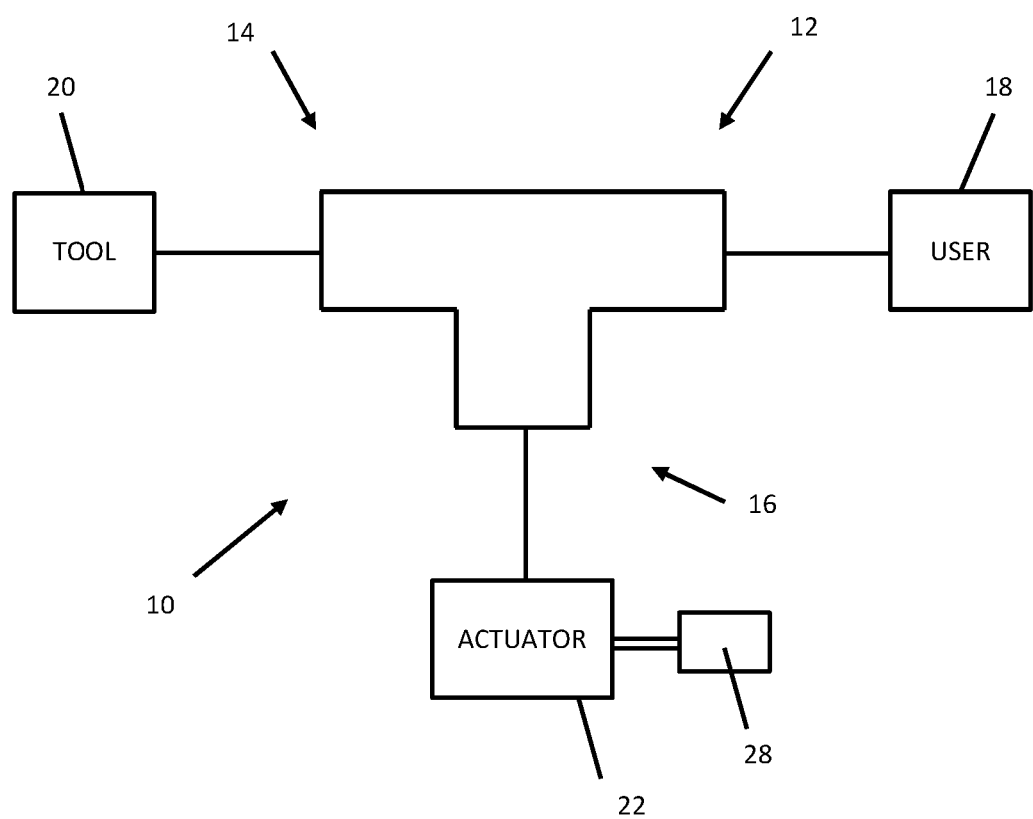
FIG. 2 shows a micromanipulator apparatus including the transmission system of FIG. 1.

As shown in FIG. 2, the input force $F_{IN}$ transmitted by the first piston 12 can be generated by a user 18 such as a surgeon. The transmission system 10 can be utilised to control a tool 20 such as a surgical instrument, in some cases the surgical instrument may be an instrument for minimally invasive or laparoscopic surgery. The ability to eliminate tremor from the surgeon's hands whilst scaling the motion and/or force of the output piston offers significant improvements in the accuracy and safety of such surgical procedures.

The modulating force $F_{IN}$ transmitted by the modulator piston 16 is controlled by an actuator 22. The actuator 22 should provide sufficient force and displacement to the modulator piston 16, according to the equations derived below for different working modes of the system.

The actuator 22 is driven by a motor 28. For safety reason, the motor 28 should be a non-back-drivable mechanism. Thus, in the event that the motor 28 stops working and the modulator piston 16 can no longer be actuated, the transmission system 10 will become a traditional mechanical hydraulic interface, working to transmit the input force $F_{IN}$ to an output force $F_{OUT}$ without any modulation.

Figure 3:
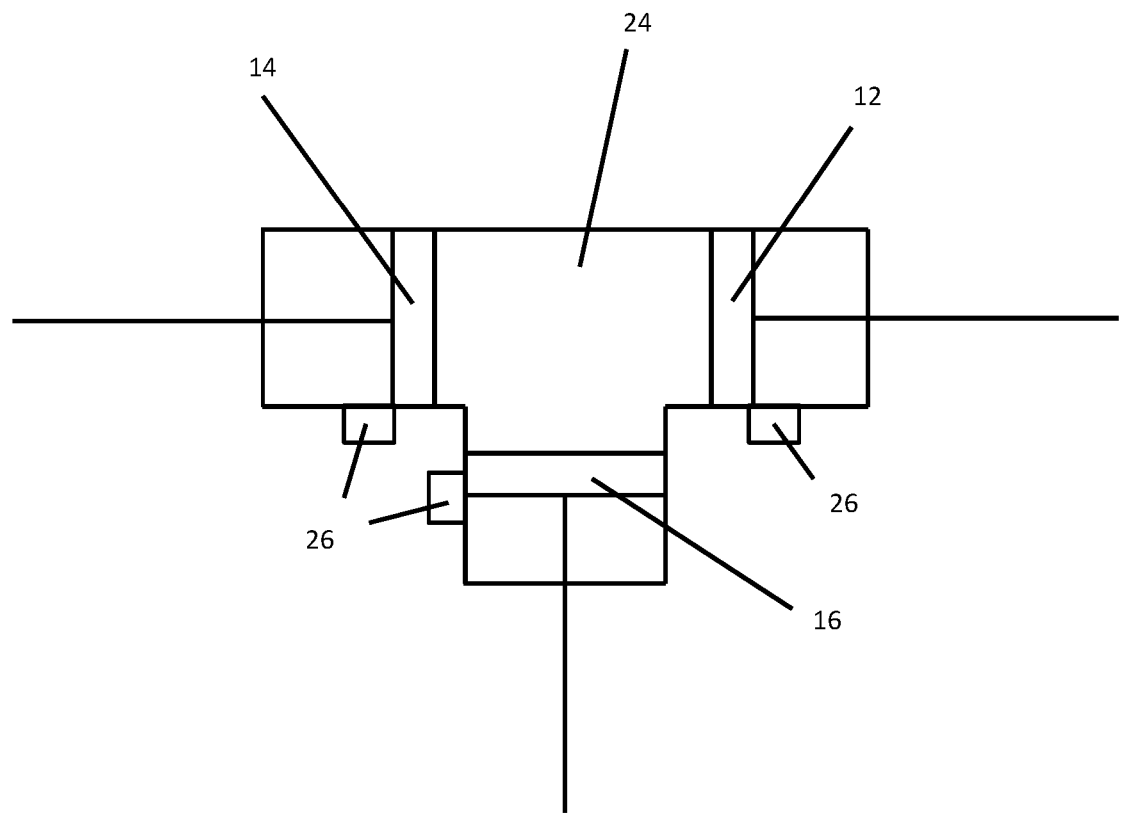
FIG. 3 is a schematic internal view of the transmission system shown in FIG. 1.

Referring to FIG. 3 of the accompanying drawings, between each of the pistons is a sealed fluid volume 24. The output force $F_{OUT}$ transmitted by the second piston 14 is generated by the first piston 12 and the modulator piston 16 transmitting forces to the sealed fluid volume 24. The transmission system 10 can operate in different working modes. In a basic working mode, the modulator piston 16 is "off" and remains in a fixed position; therefore the input force $F_{IN}$ produced by the user 18 is directly transmitted to the output force $F_{OUT}$. If both the input force $F_{IN}$ and the modulating force $F_{ACT}$ are applied to the sealed fluid volume 24 by the first piston 12 and modulator piston 16 respectively, the output force $F_{OUT}$ will be a resultant force the depends on the enhancement of the input force $F_{OUT}$ by the modulating force $F_{ACT}$. In a tremor cancellation working mode, the modulator piston 16 is actuated to apply the modulating force $F_{ACT}$ such that any tremor produced by the user 18 in generating the input force $F_{IN}$ is cancelled or mitigated in the output force $F_{OUT}$. In a motion scale working mode, the modulator piston 16 is actuated to apply a force $F_{ACT}$ to the sealed fluid volume 24 such that the input force $F_{IN}$ generated by the user 18 is variably scaled to the output force $F_{OUT}$. In a motion scale and tremor cancellation working mode, the modulator piston 16 is actuated to apply the modulating force $F_{ACT}$ to the sealed fluid volume 24 such that the input force $F_{IN}$ is modulated to both cancel tremor and scale motion.

Sensors can be used to monitor the output force $F_{OUT}$, thereby allowing improved control precision. The modulation of the input force $F_{IN}$ can be controlled according to the sensed output force $F_{OUT}$ to avoid any excess forces resulting in damage to the tool 20 connected to the second piston 14.

The position of each piston is measured to implement the control of the modulator piston 16. Equations for the control of the modulator piston 16 in the previously described working modes are derived below. Embedded position sensors 26 would be suitable for measuring the position of each piston. For example each sensor may be, a magnetic sensor, or a linear encoder. Sensors can also be provided to measure the pressure and temperature of the working fluid can also improve the performance of the control, due to the relationship of the parameters to the fluid viscosity.

If external forces are applied to the second piston 14 and transmitted to the sealed fluid volume, a force corresponding to those external forces will be transmitted through the first piston 12. As a result of this, the user 24 will "feel" any external forces applied to the second piston, $F_{OUT}$, and adjust the input force, $F_{IN}$, accordingly. The transmission system is a cheap alternative solution to an expensive master slave manipulator. The transmission system can sense external forces and provide haptic feedback without the use of any complex systems of sensors and actuators.

For the purpose of deriving the control equations, the sealed fluid volume 24 is considered to be incompressible. This is a valid assumption due to the small amount of fluid.

Figure 4:
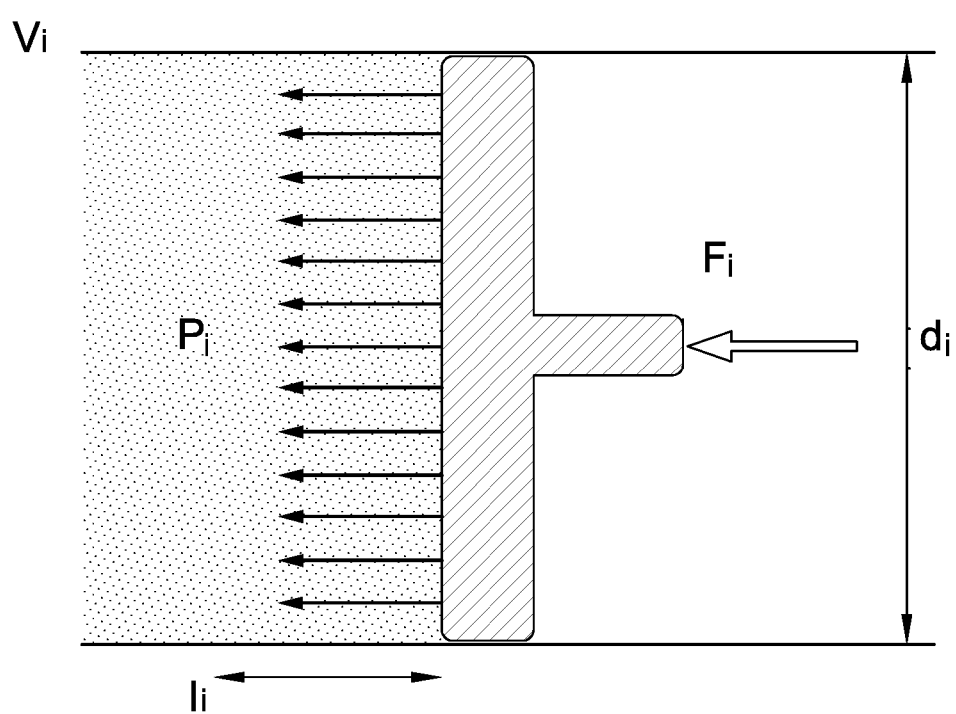
FIG. 4 shows a schematic view of a piston of the transmission system shown in FIG. 1.

FIG. 4 shows parameters for a piston. The system design requirements are the displacement $I_i$ and force $F_i$ provided to the sealed fluid volume by the piston. The static behaviour of the system is described by the following equations:

$$S_i = \frac{\pi}{4}d_i^2 \quad (2.1)$$

$$P_i = \frac{F_i}{S_i} \quad (2.2)$$

where $S_i$ is the cross-section area of the piston, $P_i$ is the pressure of the sealed fluid volume, $F_i$ is the force applied, $d_i$ is the diameter, and $I_i$ is the displacement of the piston.

The volume of fluid moved by a piston is as follows:

$$V_i = S_i l_i \quad (2.3)$$

Assuming the sealed fluid volume remains constant, the system can be described by the following equation:

$$\Sigma_{n=1}^{3} V_i = V_{IN} + V_{OUT} + V_{ACT} = 0 \quad (2.4)$$

By using equations 2.1 and 2.3, equation 2.4 becomes:

$$\sum_{n=1}^{3} V_i = \sum_{n=1}^{3} S_i l_i = \sum_{n=1}^{3} \frac{\pi}{4} d_i^2 l_i = 0 \quad (2.5)$$

$$d_{IN}^2 l_{IN} + d_{ACT}^2 l_{ACT} + d_{OUT}^2 l_{OUT} = 0 \quad (2.6)$$

$$-l_{OUT} = \frac{d_{IN}^2}{d_{OUT}^2} l_{IN} + \frac{d_{ACT}^2}{d_{OUT}^2} l_{ACT} \quad (2.7)$$

The displacement, $I_{OUT}$, of the second piston 14 is the sum of the displacements $I_{IN}$ of the first piston 12 and the displacement $I_{ACT}$ of the modulator piston 16 multiplied by the ratio of the diameter of the pistons.

When the modulator piston 16 is off, the transmission system functions as a standard hydraulic system. The input force $F_{IN}$ applied by the user 18 is transmitted to the second piston 14.

$$-l_{OUT} = \frac{d_{IN}^2}{d_{OUT}^2} l_{IN} \quad (2.8)$$

$$F_{OUT} = \frac{d_{OUT}^2}{d_{IN}^2} \quad (2.9)$$

The relation between the displacement $I_{OUT}$ of the second piston 14 and the displacement $I_{IN}$ of the first piston 12 is described by equation 2.8 and the relation between the forces $F_{OUT}$ and $F_{IN}$ is described by equation 2.9.

When the modulator piston 16 is on, the transmission system can enhance the output force $F_{OUT}$ and therefore cancel tremors in the displacement $I_{OUT}$ of the second piston 14 produced by an uneven force $F_{IN}$. Equation 2.7 describes the relation between the displacement provided by both the first piston 12 and the modulator piston 16, to the output piston. The pressure $P_{ACT}$ provided by the modulator piston 16 has to be equal to the pressure provided by both the first piston 12 and second piston 14:

$$P_{ACT} = P_{IN} + P_{OUT} \quad (2.10)$$

combining equations 2.10 and 2.2 gives:

$$\frac{F_{ACT}}{S_{ACT}} = \frac{F_{IN}}{S_{IN}} + \frac{F_{OUT}}{S_{OUT}} \quad (2.11)$$

The force $F_{ACT}$ provided by the modulator piston 16 is as follows:

$$F_{ACT} = \frac{S_{ACT}}{S_{IN}} F_{IN} + \frac{S_{ACT}}{F_{OUT}} F_{OUT} = \quad (2.12)$$

$$\frac{d_{ACT}^2}{d_{IN}^2} F_{IN} + \frac{d_{ACT}^2}{d_{OUT}^2} F_{OUT} = d_{ACT}^2 \left( \frac{F_{IN}}{d_{IN}^2} + \frac{F_{OUT}}{d_{OUT}^2} \right)$$

Equation 2.12 describes the relation between the force provided by the first piston 12 and the second piston 14 to the modulator piston 16. In order to cancel tremor, the displacement, $I_{IN}$, of the first piston 12 can be described by using a Fourier transformation:

$$l_{IN} = \sum_{k=0}^{\infty} l_{INk} e^{j2\pi f_0 t} = l_{IN0} + \sum_{k=1}^{\infty} l_{INk} e^{j2\pi k f_0 t} = l_{IN0} + l_{INTR} \quad (2.13)$$

Where $I_{IN0}$ is the continuous component of the displacement $I_{IN}$ of the first piston 12, the tremor component of the displacement $I_{IN}$ of the first piston 12 is:

$$l_{INTR} = \sum_{k=1}^{\infty} l_{INk} e^{j2\pi k f_0 t} \qquad (2.14)$$

From a consideration of equation (2.12), the modulator piston 16 needs to provide an opposite displacement to the one provided by the tremor component $I_{INTR}$ of the displacement $I_{IN}$ of the first piston 12, in order to avoid transmittal of the tremor to the second piston 14. By combining equations 2.7 and 2.14, the displacement $I_{OUT}$ of the second piston 14 is described by the following equation:

$$-l_{OUT} = \frac{d_{IN}^2}{d_{OUT}^2}(l_{IN0} + l_{INTR}) + \frac{d_{ACT}^2}{d_{OUT}^2} l_{ACT} \qquad (2.15)$$

The modulator piston 16 needs to cancel the tremor component $I_{INTR}$ of the displacement $I_{IN}$ of the first piston 12, which is described by the following equation:

$$\frac{d_{IN}^2}{d_{OUT}^2} l_{INTR} + \frac{d_{ACT}^2}{d_{OUT}^2} l_{ACT} = 0 \qquad (2.16)$$

$$\frac{d_{ACT}^2}{d_{OUT}^2} l_{ACT} = -\frac{d_{IN}^2}{d_{OUT}^2} l_{INTR} \qquad (2.17)$$

$$l_{ACT} = -\frac{d_{IN}^2}{d_{ACT}^2} l_{INTR} \qquad (2.18)$$

Equations 2.12 and 2.18 describe a compromise in the choice of the diameter $d_{ACT}$ of the modulator piston 16. The modulating force $F_{ACT}$ is directly proportional to the diameter $d_{ACT}$ of the modulator piston 16, although the displacement $I_{ACT}$ of the modulator piston 16 is inversely proportional to diameter $d_{ACT}$ of the modulator piston 16. The tremor component, $I_{INTR}$, of the displacement $I_{IN}$ of the first piston 12 is the second of the continuous component $I_{IN0}$ of the displacement $I_{IN}$ of the first piston 12 which implies that the displacement $I_{ACT}$ of the modulator piston 16 necessary to cancel the tremor is less that the total displacement $I_{IN}$ of the first piston 12.

Motion scale increases user dexterity so that operations can be performed in small scale. The motion is scaled by a factor K, which is represented by the following equation:

$$K = \frac{l_{sc}}{l_{IN}} \qquad (2.19)$$

$I_{SC}$ is the scaled input displacement. When K=1, the motion is not scaled, and when K=0.5, the motion is scaled by a ratio 1:2. The ratio between the diameter $d_{IN}$ of the first piston 12 and the diameter $d_{OUT}$ of the second piston 14 represents a motion scaling which is typical in any hydraulic system. The following equation describes the motion scaled by factor K.

$$-l_{OUT} = K \frac{d_{IN}^2}{d_{OUT}^2} l_{IN} \qquad (2.20)$$

Adding and removing the displacement $I_{IN}$ of the first piston 12, the equation remains invariant:

$$-l_{OUT} = (l_{IN} - l_{IN} + K l_{IN}) \frac{d_{IN}^2}{d_{OUT}^2} \qquad (2.21)$$

$$-l_{OUT} = l_{IN}(K-1) \frac{d_{IN}^2}{d_{OUT}^2} + l_{IN} \frac{d_{IN}^2}{d_{OUT}^2} \qquad (2.22)$$

By multiplying and dividing for the same quantity, $$\frac{d_{IN}^2}{d_{OUT}^2},$$

the equation becomes:

$$-l_{OUT} = l_{IN}(K-1) \frac{d_{IN}^2}{d_{ACT}^2} \frac{d_{IN}^2}{d_{OUT}^2} \frac{d_{ACT}^2}{d_{IN}^2} + l_{IN} \frac{d_{IN}^2}{d_{OUT}^2} \qquad (2.23)$$

$$-l_{OUT} = l_{IN}(K-1) \frac{d_{IN}^2}{d_{ACT}^2} \frac{d_{ACT}^2}{d_{OUT}^2} + l_{IN} \frac{d_{IN}^2}{d_{OUT}^2} \qquad (2.24)$$

From equations 2.7 and 2.24 it is evident that the displacement $I_{ACT}$ of the modulator piston 16 is described by the following additional equation:

$$l_{ACT} = l_{IN}(K-1) \frac{d_{IN}^2}{d_{ACT}^2} l_{IN} \qquad (2.25)$$

The equations 2.24 and 2.25, describe the relation between the displacement $I_{ACT}$ of the modulator piston 16 and the scale factor K. When K=1, the motion is not scaled, and the equation becomes:

$$-l_{OUT} = l_{IN} \frac{d_{IN}^2}{d_{OUT}^2} \qquad (2.26)$$

which describes a normal system with only two pistons.

Both the tremor cancelation and motion scale modalities can be active together. From equations 2.13, 2.18 and 2.25 the equation of the displacement $I_{ACT}$ of the modulator piston 16 is:

$$l_{ACT} = (l_{IN0}(K-1) - l_{INTR}) \frac{d_{IN}^2}{d_{ACT}^2} \qquad (2.27)$$

This equation shows that the displacement $I_{ACT}$ of the modulator piston 16 in the combined modality when the motion is scaled and tremor is cancelled, is higher than its displacement $I_{ACT}$ in the modality where only the tremor is cancelled.

The transmission system 10 is a compact and simple system composed of a minimum of three pistons and position sensors. More pistons and/or sensors may be included in the transmission system.

It will be recognised that embodiments of the transmission system thus provide a number of benefits over conventional systems.

Embodiments of the transmission system beneficially permit the ratio of the input force to the output force and the resulting relative motion of the input piston and the output piston to be scaled, whilst also cancelling or at least mitigating the effect of a tremor applied to the input piston or otherwise contained in the input force applied to the input piston. Embodiments of the transmission system thus provide significant improvements in the accuracy and safety of surgical procedures, and may permit surgical procedures to be carried out where such procedures were previously not possible due to the effects of tremors.

Moreover, the system may provide a cheap alternative solution to conventional master slave manipulators. The transmission system can sense the output force and provide haptic feedback without the use of a complex system of sensors and actuators.

Various modifications may be made without departing from the scope of the claims.

The invention claimed is:

1. A hydraulic transmission system for use in a micromanipulator system, comprising:
    an input actuator comprising an input piston, the input piston configured to receive an input force;
    a control actuator comprising a modulator piston, the modulator piston operatively associated with the input piston and configured to apply a modulating force to modulate the input force;
    an output actuator comprising an output piston, the output piston operatively associated with the first piston and the modulator piston, the output piston configured to receive the modulated input force and output an output force from the transmission system; and
    a control system comprising one or more position sensor associated with the input actuator, output actuator and control actuator, wherein the control system is configured to control the control actuator according to the sensed position of the input piston, the output piston and the modulator piston to vary the ratio of the input force to the output force up or down by reconfiguring the control actuator so as to permit the effect of a tremor contained within the input force to be cancelled, mitigated or otherwise controlled within a given acceptable range.

2. The transmission system of claim 1, wherein the transmission system is configured to modulate the input force by attenuating or dampening the input force to provide a reduced output force and/or reduced displacement of the output piston.

3. The transmission system of claim 1, wherein the transmission system is configured to modulate the input force to provide an increased output force from the output piston and/or increased displacement of the output piston where required.

4. The transmission system of claim 1, wherein the transmission system is configured to modulate the input force in response to a force applied to the modulator piston.

5. The transmission system of claim 1, wherein the control actuator is reconfigurable to extend the modulator piston, extension of the modulator piston modulating the input force by decreasing the input force, thereby providing a reduced modulated input force to the output piston.

6. The transmission system of claim 1, wherein the control actuator is reconfigurable to retract the modulator piston retraction of the modulator piston modulating the input force by increasing the input force, thereby providing an increased modulated input force to the output piston.

7. The transmission system of claim 1, wherein the transmission system is configured to maintain the ratio of the input force to the output force at a given value or value range.

8. The transmission system of claim 1, wherein the transmission system comprises a drive arrangement configured to move and/or control the displacement of the modulator piston.

9. The transmission system of claim 8, wherein the drive arrangement comprises a motor.

10. An apparatus comprising the transmission system of claim 1.

11. The apparatus of claim 10, further comprising an instrument, and wherein the output piston is coupled to the instrument and is configured to transfer the output force to the instrument.

12. The apparatus of claim 11, wherein the instrument comprises a surgical instrument.

13. A method comprising:
    providing a transmission system according to claim 1;
    applying a modulating force to the modulating piston to modulate the input force received by the output piston.

14. The transmission system of any preceding claim, comprising a sealed chamber for containing substantially incompressible hydraulic fluid so as to define a sealed fluid volume, the sealed chamber configured to communicate with the input piston, the output piston and the modulator piston, such that external forces applied to the output piston are transmitted via the sealed fluid volume to the input piston so as to provide haptic feedback from the output piston at the input piston.

15. The transmission system of claim 14, comprising at least one of:
    one or more pressure sensors configured to measure the fluid pressure in the chamber; and
    one or more temperature sensors configured to measure the temperature in the chamber.

* * * * *

UNITED STATES PATENT AND TRADEMARK OFFICE
CERTIFICATE OF CORRECTION

PATENT NO. : 11,255,352 B2  
APPLICATION NO. : 16/618648  
DATED : February 22, 2022  
INVENTOR(S) : Luigi Manfredi Page 1 of 1

It is certified that error appears in the above-identified patent and that said Letters Patent is hereby corrected as shown below:

On the Title Page

(30) Foreign Application Priority Data: Please correct "1708807" to read -- 1708807.1 --

In the Specification

Column 5, Line 65: Please correct "$\Sigma_{n=1}^{3} V_i = V_{IN} + V_{OUT} + V_{ACT} = 0$" to read -- $\sum_{n=1}^{3} V_i = V_{IN} + V_{OUT} + V_{ACT} = 0$ --

Column 6, Line 65: Please correct "$I_{IN} = \sum_{k=0}^{\infty} I_{INk} e^{j2\pi f_0 t} = I_{IN0} + \sum_{k=1}^{\infty} I_{INk} e^{j2\pi k f_0 t} = I_{IN0} + I_{INTR}$" to read -- $I_{IN} = \sum_{k=0}^{\infty} I_{INk} e^{j2\pi f_0 t} = I_{IN0} + \sum_{k=1}^{\infty} I_{INk} e^{j2\pi k f_0 t} = I_{IN0} + I_{INTR}$ --

Column 7, Line 6: Please correct "$I_{INTR} = \sum_{k=1}^{\infty} I_{INk} e^{j2\pi k f_0 t}$" to read -- $I_{INTR} = \sum_{k=1}^{\infty} I_{INk} e^{j2\pi k f_0 t}$ --

Signed and Sealed this  
Fifth Day of July, 2022

*Katherine Kelly Vidal*

Katherine Kelly Vidal  
*Director of the United States Patent and Trademark Office*